United States Patent [19]

Schmidt

[11] 4,023,096
[45] May 10, 1977

[54] METHOD AND APPARATUS FOR DETERMINING PHYSICAL CHARACTERISTICS OF EMULSIONS

[75] Inventor: Thomas R. Schmidt, Houston, Tex.

[73] Assignee: Shell Oil Company, Houston, Tex.

[22] Filed: Feb. 17, 1976

[21] Appl. No.: 658,933

[52] U.S. Cl. .................... 324/61 R; 23/230 A; 23/253 A; 204/1 T; 204/195 R; 137/2; 137/88
[51] Int. Cl.² ........................................ G01R 27/26
[58] Field of Search ............ 324/61 R, 61 P, 30 R; 137/2, 88; 204/164, 195 R, 1 T, 275; 23/230 A, 253 A

[56] References Cited

UNITED STATES PATENTS

| | | | |
|---|---|---|---|
| 3,665,301 | 5/1972 | Maltby | 324/61 P |
| 3,757,210 | 9/1973 | Hansen et al. | 324/61 R |

*Primary Examiner*—Stanley T. Krawczewicz

[57] ABSTRACT

A method and automatic apparatus for determining the physical properties of an emulsion wherein a sample of the emulsion is allowed to settle in a sample cell formed by a capacitor. The interface level, as emulsion breaks and settles to its final value, is followed by measuring the cell capacity.

8 Claims, 4 Drawing Figures

METHOD AND APPARATUS FOR DETERMINING PHYSICAL CHARACTERISTICS OF EMULSIONS

BACKGROUND OF THE INVENTION

In many chemical processes it is desirable to know the property of an emulsion, for example, in an alkylation process in a refinery, it is desirable to know the properties of the acid emulsion. In an alkylation process it is important to know the strength or settling time of the emulsion as well as the percentage of acid remaining in the system. The settling time is required to control the recycle rate of the acid while the quantity of acid determines the amount of make-up acid to be added to the process.

In the past, it has been customary to obtain a small sample of the alkylation emulsion in a sight glass and allow it to stand until the acid settles. By manually timing the settling and visually observing the percentage of acid on the emulsion, one obtained the necessary information. Based on these physical measurements, the alkylation process could then be adjusted to obtain optimum results. While this approach has been satisfactory in past operations, it is desirable to convert more of the process to automatic control. In order to obtain optimum results from any automatic control, it is necessary to have information on the physical properties of the emulsion.

BRIEF DESCRIPTION OF THE INVENTION

The present invention solves the above problems by providing a simple automatic apparatus for obtaining the settling time or strength of the emulsion and the percentage of the components in the system. More particularly, the invention utilizes a settling cell for holding a fixed amount of the emulsion and allowing it to settle. The plates of a capacitor are disposed in the settling cell so that as the emulsion separates relative proportional areas of both of the plates are exposed to the components of the emulsion. For example, in the case of a gravity type settling cell, the cell could be cylindrical with the outer wall forming one plate of the capacitor and a central electrode forming the second plate. Thus, as the emulsion breaks and settles, an equal length of both electrodes will be exposed to components.

An alternate settling cell can be formed by a centrifuge which will decrease the time required to separate the emulsion. In the case of a centrifuge, the horizontal surface of the rotating cup could form one electrode of the capacitor while the second electrode of the capacitor is placed parallel to and spaced from the rotating cup.

In both of the above types of cells when measuring the characteristics of an emulsion having one component that is a conductor, it is necessary to insulate one of the electrodes with a suitable material. For example, it has been found satisfactory to cover the center electrode in the case of a cylindrical gravity settling cell or the rotating disc in the case of a centrifuge type cell with a coating of a polytetrafluoroethylene polymer sold under the tradename Teflon. The strength of one component as well as the settling time of the emulsion is determined by measuring the capacitance of the cell. The capacitance will vary exponentially and reach a steady state condition which will remain substantially constant. The time required for the capacitance to reach the steady state condition will be the settling time for the emulsion while the magnitude of the capacitance in its steady state condition will be related to the acid strength of the emulsion. When a centrifuge is used as the settling cell, the settling will be considerably reduced but will still be related to the time for the emulsion to settle by gravitational forces. Thus, the same type of capacitance curve will be obtained and it can be correlated with the settling time and acid strength of the emulsion.

BRIEF DESCRIPTION OF THE DRAWINGS

The present invention will be more easily understood from the following detailed description when taken in conjunction with the attached drawings, in which.

PREFERRED EMBODIMENTS

Figure 1:
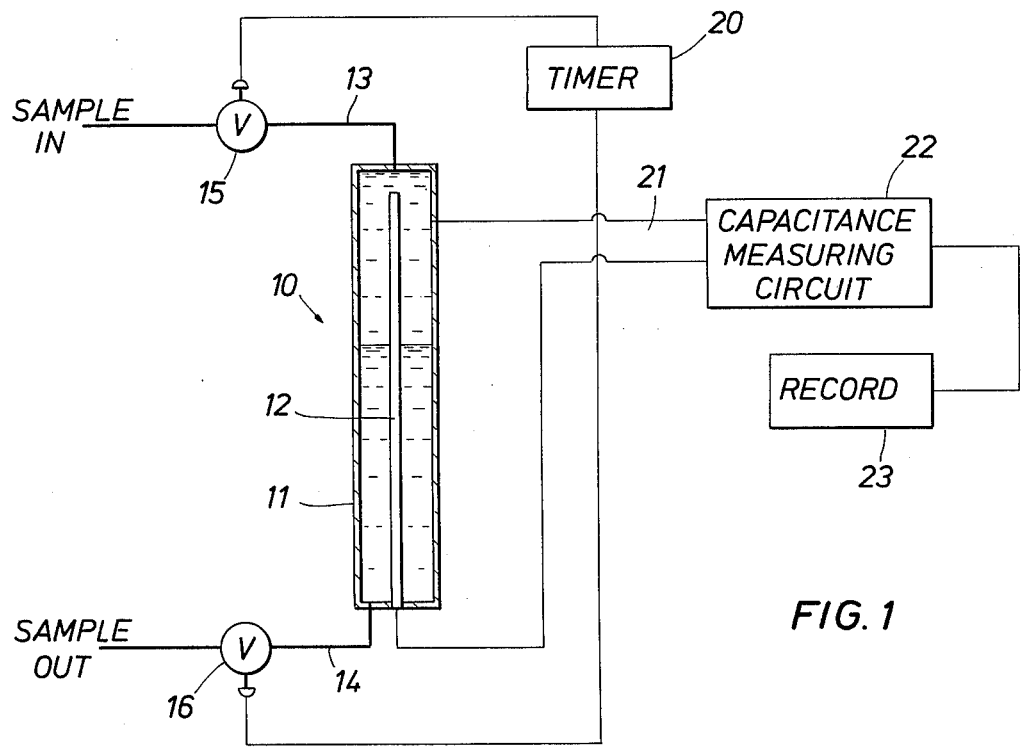
FIG. 1 is a schematic illustration of one form of the invention.

Referring now to FIG. 1, there is shown an embodiment of the invention utilizing a settling cell in which the emulsion is allowed to settle by gravity. The settling cell 10 comprises an elongated cylindrical housing having an outer wall 11 closed at both ends. The cylindrical housing should be formed of a good electrical conducting material such as stainless steel or the like. Disposed within the housing is a central electrode 12 which with the outer wall of the housing forms the capacitor. Due to the electrical conductivity of the acids present in alkylation emulsions, it is necessary to coat one of the electrodes preferably the central electrode with a material having a high dielectric constant, for example, the central electrode may be coated with a polytetrafluoroethylene polymer sold under the tradename Teflon.

The settling cell should be provided with an inlet 13 and an outlet 14 with the inlet having a suitable flow control means 15 and a flow control means 16 being provided in the outlet. Preferably, the flow control means are pneumatically or electrically operated valves so that they may be controlled by a timing means 20. The timer 20 is programmed to open the outlet and inlet in the cell to produce a flow through the cell at periodic intervals and then close both the inlet and outlet to retain a fixed amount of emulsion within the cell. The duration of the flow through the cell should be chosen so that the cell is completely flushed and the retained sample of the emulsion is representative of the emulsion whose settling time and acid content is desired.

The central electrode and outer shell of the settling cell are coupled by means of leads 21 to a capacity measuring circuit 22. The capacity measuring circuit may be any well known type of capacity measuring device, for example, Robertshaw "Level-Tel" sold by Robertshaw Controls Company, Anaheim, Calif. The output of the capacity measuring circuit is supplied to a chart recorder 23 which is preferably a clock driven type having a continuous chart record. The capacity measuring circuit and chart record are operated continuously so that the fill time of the cell as well as the time for settling and the acid content of the emulsion are recorded.

Figure 2:
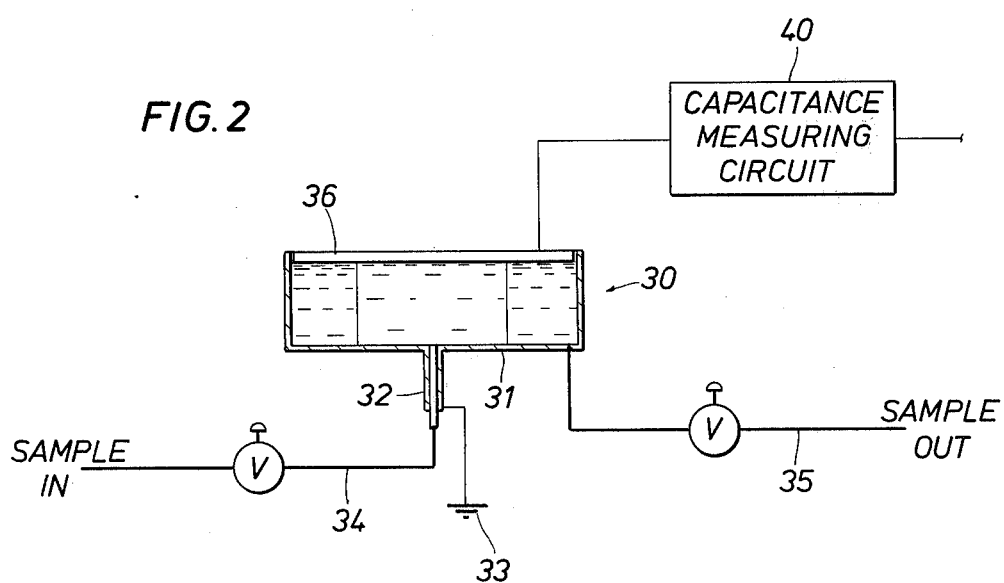
FIG. 2 is an illustration of the second embodiment of the invention.

Referring now to FIG. 2, there is shown a modified form of the invention in which the gravity settling cell of FIG. 1 is replaced by a centrifuge 30. The cup member 31 of the centrifuge is mounted on a shaft 32 which is grounded at 33. The centrifuge is provided with an inlet 34 and an outlet 35 having suitable control valves disposed therein. Positioned above the cup member and substantially parallel to the bottom is a plate 36 which with the cup member forms the capacitor of the measuring circuit. The plate 36 is coupled to a capacitance measuring means 40 which is similar to the capacity measuring means 22 of FIG. 1.

While the centrifuge shown in FIG. 2 is shown in a simplified form, obviously a suitable rotating member can be used as one plate of the capacitor while the fixed plate can be mounted in the centrifuge and disposed to form a capacitor. The rotating member should preferably be coated with the polymer as the central electrode of the settling cell shown in FIG. 1. Likewise, the ground connection shown for the centrifuge can normally be the case of the centrifuge since the shaft supporting the rotating member will be effectively grounded to the case of the centrifuge. The use of the centrifuge as explained above has the advantage of providing quicker settling times for the emulsion and thus providing more frequent measurements than are possible with the settling cell of FIG. 1. Of course, when a centrifuge is used, it will be necessary to correlate the readings obtained from the chart recorder to the actual settling times of the emulsion.

Operation

Figure 3:
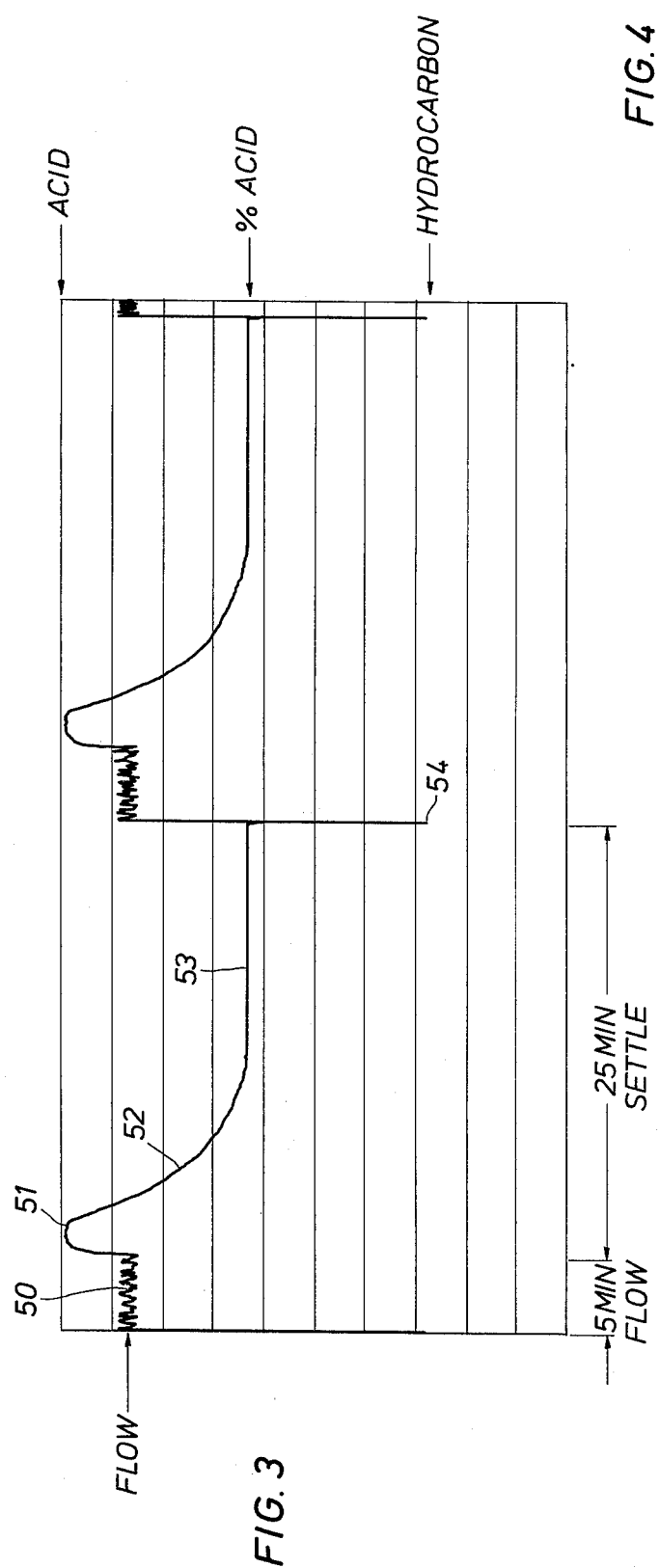
FIG. 3 is a portion of a chart record from the apparatus of the present invention.

When either of the cells shown in FIGS. 1 and 2 are operated, it is necessary to supply a sample to the cell for a sufficient period of time to completely flush the cell and provide a representative sample. In practice, it has been found that a flow of five minutes through the cell shown in FIG. 1 will normally supply a representative sample to the cell. After the cell has been flushed, the inlet and outlet valves are closed to retain a fixed amount of the emulsion within the settling cell. FIG. 3 illustrates the response of the cell illustrated in FIG. 1 to the emulsion from an alkylation process. The capacitance will then increase up to a quantity indicating almost 100 percent acid in the cell as shown by the portion 51 of the curve of FIG. 3. After a short interval of time, the capacitance of the cell will decrease in the substantially exponential fashion as shown by the portion 52 of FIG. 3. The capacitance then will reach some steady state value and continue until the cell is flushed by initiating a new flow of sample through the cell. This constant capacitance as shown by the portion 53 of FIG. 3 is representative of the acid content of the emulsion. The scale of the chart shown in FIG. 3 can be calibrated directly in percent/acid of the emulsion if desired. As a new flow through the cell is initiated, the capacitance of the cell will decrease in a rapid manner as shown by the spike 54 of the recording in FIG. 3. This is the result of the hydrocarbon which has settled from the previous sample being flushed through the cell and decreasing the capacitance of the cell.

From the time base shown in FIG. 3, one can compute the settling time for the emulsion. Similarly, from the magnitude of the capacitance of the cell, one can compute the acid content of the emulsion. Once a sample cell is calibrated both the settling time and acid strength can be obtained automatically by simple instrumentation. For example, when the flow through the cell is stopped, a suitable timing circuit can be started with the timing circuit being stopped when the value of the capacitance no longer changes. The steady state of the capacitance measurement can easily be determined by suitable comparing circuits having relatively short time constants. Of course, the amplitude or magnitude of the measured capacitance and steady state can be used directly as a measurement of the acid content of the emulsion.

Figure 4:
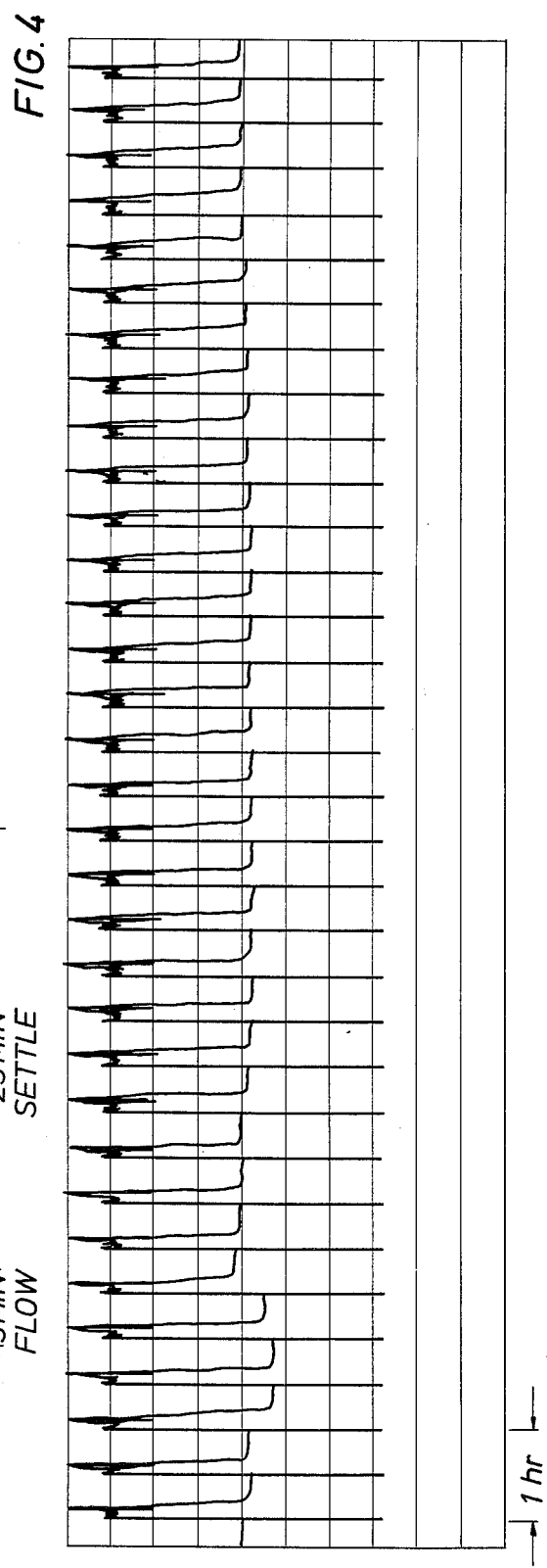
FIG. 4 is a portion of a second chart record from the apparatus of the present invention.

Referring to FIG. 4, there is shown the same information as shown on the record of FIG. 3 but with the time base considerably compressed. By compressing the time base, one can observe a trend in the acid content of the emulsion. Since in alkylation processes, it is the trend or change in the acid content over a long period of time which is important, one can obtain the information from FIG. 4 visually if one so desired. Of course, it is also a simple matter to utilize the magnitude of the capacitance measurement shown in FIG. 4 for controlling the alkylation reactor as explained above.

While the above description of the data recorded in FIGS. 3 and 4 has been in terms of acid and hydrocarbon emulsion, it should be obvious that the device will work as well with any two materials that have differing dielectric constants and will separate by gravity or centrifuging. Moreover, geometry of the cell can be modified to accentuate small amounts of material collecting at the top or bottom of the cell during the settling process. This can be accomplished for the cell shown in FIG. 1 by using a smaller diameter for the portion of the cell in which the desired material is concentrated.

I claim as my invention:

1. A method for determining the settling time and percent of constituents in an emulsion comprising:
    placing a fixed quantity of the emulsion in a closed cell;
    retaining the fixed quantity of emulsion in the cell while separating the emulsion into its individual constituents; and
    measuring the capacity of the cell as the emulsion constituents separate the time required for the cell capacity to reach a steady state being related to the settling time of the emulsion and the magnitude of the steady state capacity being related to the percent of constituents in the emulsion.

2. The method of claim 1 wherein said capacity of the cell is measured between capacitor plates disposed to expose equal relative areas to the constituents of emulsion as they separate.

3. The method of claim 1 wherein the emulsion is an alkylation emulsion.

4. An apparatus for determining the settling time and percentage of constituents in an emulsion comprising:
    a closed cell adapted to retain a fixed quantity of the emulsion;
    fluid supply means communicating with said cell to supply said fixed quantity of the emulsion to the cell;
    a pair of capacitor electrodes, said electrodes being disposed in the cell so that equal relative areas are exposed to the constituents of the emulsion as the emulsion constituents separate; and
    measuring means, said measuring means being coupled to said capacitor electrodes to measure the capacitance of the cell with respect to time as the emulsion settles.

5. The apparatus of claim 4 wherein said cell comprises a vertical cylindrical cell.

6. The apparatus of claim 5 wherein said capacitor electrodes comprise the outer wall of said cell and a center electrode, said center electrode being coated with a material having a high dielectric constant.

7. The apparatus of claim 4 wherein said cell comprises a centrifuge.

8. The apparatus of claim 7 wherein the electrodes of said capacitor comprises a rotating element of the centrifuge and a fixed plate, said fixed plate being spaced from said rotating element.

* * * * *